(12) United States Patent
Peters, III

(10) Patent No.: US 6,616,638 B2
(45) Date of Patent: Sep. 9, 2003

(54) HYPODERMIC NEEDLE CAP AND SHARPS PROTECTIVE CAP EJECTOR

(75) Inventor: David Blake Peters, III, 15D Windsor Ct., Keene, NH (US) 03431

(73) Assignees: Craig J. Bell, East Swanzey, NH (US); David Blake Peters, III, Keene, NH (US)

( * ) Notice: Subject to any disclaimer, the term of this patent is extended or adjusted under 35 U.S.C. 154(b) by 0 days.

(21) Appl. No.: 09/878,852

(22) Filed: Jun. 11, 2001

(65) Prior Publication Data

US 2002/0091360 A1 Jul. 11, 2002

Related U.S. Application Data

(60) Provisional application No. 60/212,808, filed on Jun. 19, 2000.

(51) Int. Cl.$^7$ .................... A61M 5/32; A61M 5/178; A61M 5/00
(52) U.S. Cl. .................. 604/192; 604/164.08; 604/198; 604/263
(58) Field of Search .................. 604/263, 110, 604/163, 164.08, 192, 197, 198; 128/919

(56) References Cited

U.S. PATENT DOCUMENTS 4,500,312 A * 2/1985 McFarlane .................. 604/192
4,735,617 A * 4/1988 Nelson et al. .............. 604/192

* cited by examiner

*Primary Examiner*—Michael J. Hayes
*Assistant Examiner*—Catherine Serke
(74) *Attorney, Agent, or Firm*—Davis & Bujold, P.L.L.C.

(57) ABSTRACT

A removal system and method to facilitate removal of a sheath from a medical device such as a hypodermic needle. The removal system comprises a sheath having an exterior housing defining an internal cavity for accommodating a hypodermic needle therein. The sheath is open at one end thereof to facilitate receiving the hypodermic needle therein. An exterior surface of the sheath supports at least one appendage comprising at least one tension leg which interconnects a pushing surface with the sheath. The at least one tension leg partially bows, once a sufficient removal force is applied thereto, facilitating removal of the sheath from a hypodermic needle via a clinician via a one handed technique.

17 Claims, 6 Drawing Sheets

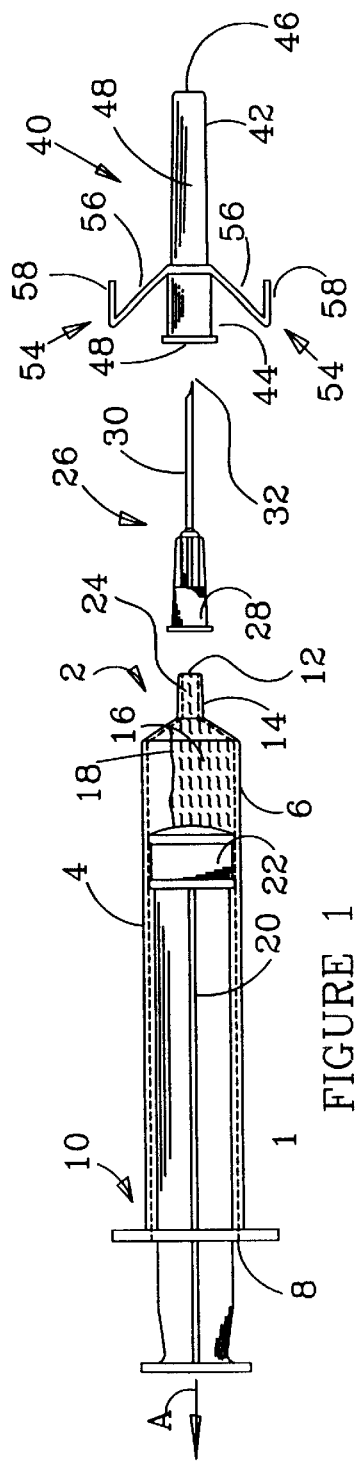
FIGURE 1
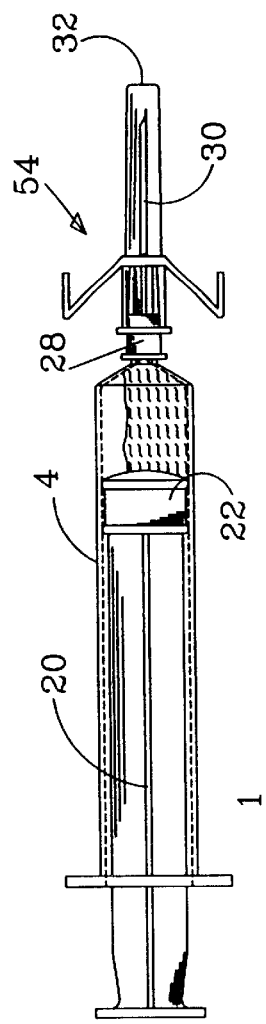
FIGURE 2
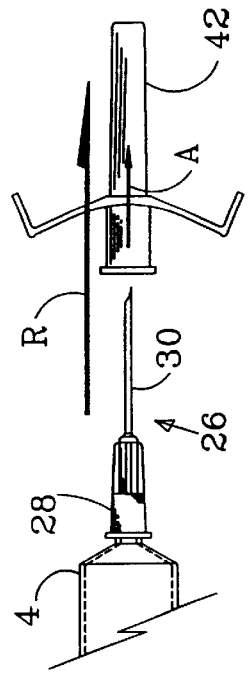
FIGURE 3A
FIGURE 3B

HYPODERMIC NEEDLE CAP AND SHARPS PROTECTIVE CAP EJECTOR

This application claims benefit of U.S. application Ser. No. 60/212,808 filed Jun. 19, 2000.

FIELD OF THE INVENTION

The present invention relates to the area of protective sheaths, and more specifically to a sheath that covers and protects a medical device, such as a hypodermic needle, and is removable therefrom without damaging the sheathed medical device, e.g. the hypodermic needle, or injuring a clinician removing the sheath.

BACKGROUND OF THE INVENTION

The use of a hypodermic needle in the medical field is well known in the art. Hypodermic needles are commonly used to deliver intravenous and intramuscular therapies, for placement of catheters, for withdrawing various body fluids, and for a multitude of other conventional procedures.

Hypodermic needles are commonly constructed from a hollow stainless steel cannula that has a proximal end connected to a standard luer taper connector and a remote distal end that is manufactured into an engineered tip or point. The manufacturers of such needles have developed sophisticated grinding techniques to generate complex tip geometries which achieve extremely sharp points. These extremely sharp points easily penetrate the skin of a patient as well as the underlying tissue(s) with only minimal discomfort to the patient and facilitate maximum control by the clinician. To reduce the drag of the hypodermic needle, during penetration with the tissue, as well as to improve comfort to the patient, manufactures will commonly treat the exterior surface of the hypodermic needle with silicone or some other lubricant.

In order to protect these rather fragile needle shafts and tips or points, as well as to protect the sterility of the hypodermic needle prior to use, a protective cap or sheath generally covers or encases the hypodermic needle. Such sheaths are commonly constructed from a plastic material such as polypropylene. The sheath surrounds, encases and encloses the hypodermic needle and is generally maintained in position by an interference fit between an inwardly facing surface of the sheath and an exterior surface of a hub supporting the hypodermic needle. Subtle variations in the needle hub and the sheaths, in addition to variations in automated assembly equipment dynamics, result in varying degrees of difficulty in removing the protective sheath from the hub to expose the hypodermic needle.

It is to be appreciated that the interference fit between the hub and the sheath must be sufficiently great to maintain engagement throughout the manufacturing, the packaging, the sterilization, and the shipping processes of the medical device. However, when a clinician desires to remove the sheath prior to use, the sheath removal force may pose a challenge to the clinician. This can translate into damaging the delicate tip or point of the hypodermic needle or possibly result in an inadvertent needle stick injury to the clinician.

The standard procedure used by clinicians for removing a sheath from a hypodermic needle is a two handed technique. That is, the clinician grabs a syringe, a catheter, or some other medical device attached to the hypodermic needle with the clinician's dominant hand (e.g. either his or her right or left hand), then with the clinician's non-dominant hand (e.g. either his or her left or right hand) pulls the sheath in an opposite direction to overcome the interference fit, between the sheath and the hub, and thus strip the sheath from the hypodermic needle. However, care should be taken to ensure that the sheath is removed parallel to the needle shaft, although this is rarely done. If the sheath is not removed parallel to the needle shaft, the sheath may contact and damage the fragile needle tip or point. Such contact can bend the tip creating either a burr, an indentation, a deformation, etc. (an "imperfection") in the end portion of the hypodermic needle. Such an imperfection results in a needle tip that will significantly increase the pain experienced by the patient during penetration and/or extrication of the hypodermic needle through the tissue. The imperfection can also increase the drag of the hypodermic needle when passing through the tissue, and this may, in turn, decrease the accuracy of the clinician. Finally, such imperfection in the tip may also create a puncture of the blood vessel that is more traumatic and may be more difficult to stop the bleeding following completion of the medical procedure.

Moreover, in many situations, the clinician's non-dominant hand is occupied by one of a variety of necessary procedures, such as securing an injection sight, holding a drug vial, palpitating and/or stabilizing a vein, attending to a need of a patient, etc. In circumstances where only one hand is available for removal of the sheath, a clinician will often resort to biting the sheath with his or her teeth and pulling the hypodermic needle away from his or her mouth. Such a sheath removal procedure places the sharp needle-point in close proximity to the clinician's face, risking possibly injury. It also places the hypodermic needle directly in a path of the inhalation and/or exhalation breath from the mouth and/or the nose of the clinician. This increases the likelihood of microbiological contamination to the hypodermic needle, just prior to use on a patient. As with any type of exertion, an involuntary "grunt" or exhalation often accompanies such effort, making needle removal by the mouth extremely unsanitary and a source of contamination to the patient.

SUMMARY OF THE INVENTION

Wherefore, it is an object of the present invention to overcome the aforementioned problems and drawbacks associated with current needle sheath removal techniques and procedures currently available in the art.

The present invention generally relates to a system and a method for removing a sheath from a hypodermic needle by utilization of a one-handed technique.

The present invention also relates to a system and a method for removing a sheath from a hypodermic needle without damaging the delicate needle tip or point of the hypodermic needle while minimizing the threat of contamination to the hypodermic needle prior to use.

The present invention, in its most basic form, relates to a needle sheath with at least one arm or appendage permanently affixed to the sheath. The at least one arm or appendage is utilized to generate a mechanical force that overcomes the friction retention force between the needle hub and the sheath. This mechanical force results in an ejection force which facilitates disengagement of the sheath from the needle hub and the needle. The mechanical force is generally applied by the fingers of the hand (e.g. the index and the thumb of a clinician) holding the sheath connected to the medical device. It is to be appreciated that the medical device could be a syringe, a catheter hub, or the like. The removal system of the present invention allows for a one-handed removal of the sheath which allows the free hand of the clinician to be involved in the patient's care or preparing a site for needle penetration, for example.

According to another embodiment of the invention, the arm or appendage incorporates a spring force that enhances the mechanical advantage required to overcome the friction retention force between the sheath and the need hub. When the interference fit is overcome by the applied force, the parts separate and the recoil of the spring propels the sheath axially along and off of the hypodermic needle. The resultant action removes the sheath in a direction that is parallel to a longitudinal axis of the hypodermic needle thereby minimizing the side forces and reducing the possibility that the sharp point will be contacted, touched or otherwise damaged during sheath removal. The hypodermic needle is then ready to be utilized on the patient via a desired medical procedure.

Another embodiment of the invention incorporates the removal means previously stated with a re-sheathing or needle protective device. This combination provides the means for safely removing the sheath using a one-handed technique, then cover or disarm the used and contaminated needle following completion of the medical procedure. Such disarming of the hypodermic needle prevents inadvertent needle sticks from a contaminated needle. It is well known that needle sticks from contaminated needles can result in diseases, such as HIV and hepatitis, being transferred to the clinician or some other care giver.

BRIEF DESCRIPTION OF THE DRAWINGS

The invention will now be described, by way of example, with reference to the accompanying drawings in which:

FIG. 1 is a diagrammatic exploded side elevational view of the improved sheath with an associated syringe and hypodermic needle;

FIG. 2 is a diagrammatic assembled side elevational view of the improved sheath coupled to a hypodermic needle which is affixed to a syringe;

FIG. 3A is a partial diagrammatic assembled side elevational view of the improved sheath coupled to a hypodermic needle just prior to the sheath removal force exceeding the sheath retention force;

FIG. 3B is a diagrammatic side elevational view showing the sheath being expelled axially along the hypodermic needle;

DETAILED DESCRIPTION OF THE INVENTION

Figure 4A:
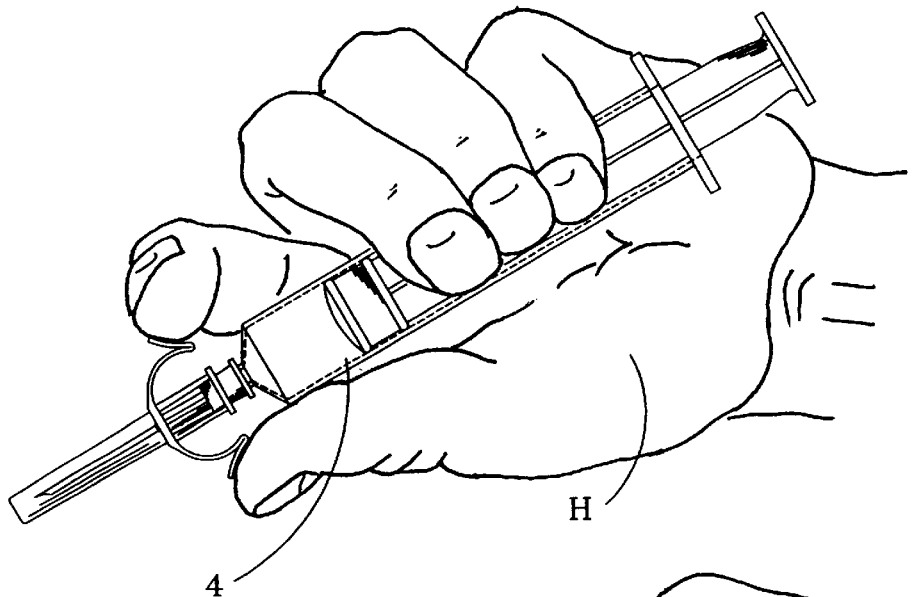
FIG. 4A is a diagrammatic perspective view showing a clinician grasping the two appendages to commence generation of a sufficient removal force for expelling the sheath axially by pinching the opposed pushing surfaces.

The present invention relates to a removal system for removing a protective sheath from a medical device such as a hypodermic needle. The sheath removal system, according to the present invention, allows removal of the protective sheath via a one handed technique that does not damage the shaft, tip or point of the hypodermic needle, does not result in contamination of the shaft, tip or point of the hypodermic needle and minimizes the possibility of injury to the clinician, or some other care giver, during removal of the protective sheath.

The following description is of a preferred embodiment of the sheath removal system and is in no way meant to limit the size, the shape or the ability of the manually or automatically operated sheath removal system. In addition, the following description is not intended to limit the type of material used in the construction of the removal system or the orientation of the various components.

Turning now to FIGS. 1–4, a detailed description concerning the various components of a prior art medical device, such as a hypodermic needle, the sheath removal system according to the present invention will now be provided. As can be seen in these Figures, the prior art medical device 2 comprises a syringe 4 having an exterior housing 6. The syringe 4 is opened 8 at a first end 10 thereof and has a fluid passage 12 at an opposed second end 14 thereof. The exterior housing 6 of the syringe 4 defines an internal cavity 16 therein for accommodating a desired product 18 to be dispensed or a sample to be withdrawn through the fluid passage 12. An associated plunger 20 is slidably accommodated within the internal cavity 16, via the opening 8, and a rubber tip 22, located at a leading end of the plunger 20, forms a fluid tight seal with the inwardly facing surface of the syringe 4. As the plunger 20 moves relative to the internal cavity 16 of the syringe 4, fluid is caused to flow through the fluid passage to facilitate either dispensing a desired product from the syringe 4 or withdrawing a desired sample into the syringe 4.

The second end 14 of the syringe 4 has a standard leur tapered male connector 24 which surrounds the fluid passage 12. It is to be appreciated that the male leur connector 24 can be either a tapered design (as shown) which utilizes a frictional connection or the male leur connector 24 may be a threaded design (not shown) which utilizes a threaded connection.

A hypodermic needle 26 comprises a hub 28 having an inwardly facing tapered surface, or possibly an internal thread, which has a mating fit with the exterior surface (or thread) of the male leur connector 24 to provide a secure connection between those two components and facilitate secure connection of the syringe 4 to the hypodermic needle 26. The hub 28 supports a hypodermic cannular shaft 30 which eventually tapers to a beveled hypodermic tip or point 32 to facilitate penetration of the hypodermic cannular shaft 30 through the skin and tissue of a patient. An elongate passageway (not shown) extends through the hub 28 and the hypodermic cannular shaft 30 to provide a fluid flow path between the hypodermic point or tip 32 and the internal cavity 16 of the syringe 4. If desired, the hub 28 may be provided with a pair of opposed locking ears (not shown) or a threaded shroud thus facilitating a secure connection of the syringe 4 to the hypodermic needle 26. As the syringe 4 and the hypodermic needle 26 are conventional and well known in the art, a further detailed description concerning the same is not provided.

The improved removal system, according to the present invention, will now be described in further detail. As can be seen in FIGS. 1–3, the removal system 40 generally comprises an exterior sheath 42 which has a proximal end 44 and an opposed distal end 46. The proximal end 44 of the sheath 42 is open 48 to facilitate receiving the hypodermic cannular shaft 30 and the hypodermic tip or point 32 therein while the opposed distal end 46 of the sheath 42 is closed. The sheath 42 is generally cylindrical in shape and defines an interior compartment 48 for accommodating the hypodermic cannular shaft 30 and hypodermic tip and point 32. The sheath 42 is sized to provide a sufficient clearance between an inwardly facing surface of the sheath 42 and an exterior surface of the hypodermic cannular shaft 30 and hypodermic tip and point 32 to prevent inadvertent damage occurring thereto.

The exterior wall of the sheath 42 typically has a thickness of between about 0.025 and about 0.500 inches or so and is manufactured from polypropylene, polyethylene, styrene, or some other conventional material which is commonly used to manufacture syringes and other medical devices. Preferably, the sheath has a diameter of between 0.050 and 0.750 inches or so and has an axial length of between 0.060 and 6 inches or so.

A pair of opposed side arms or appendages 54 are secured to the proximal end 44 of the sheath 42. Each opposed side arm or appendage 54 generally comprises a tension arm 56 and a remote pushing surface 58. Each pushing surface 58 extends substantially parallel a longitudinal axis A of the syringe 4 and the hypodermic needle 26.

When removal of the sheath 42 from the hypodermic needle 26 is desired, the clinician will grasp the combined syringe/hypodermic needle/sheath with the clinician's dominant hand H (e.g. the left hand in FIG. 4A) and place his or her thumb on one of the pushing surfaces 58 and place his or her index finger on the other pushing surface 58. Thereafter, the clinician will bias or pinch the two pushing surfaces 58 toward one another. As this inwardly directed force F (see FIG. 3A) is applied to the two pushing surfaces 58 by the clinician, such inwardly directed force F biases the pair of pushing surfaces 58 toward one another and causes the respective tension legs 56 to commence bowing (see FIG. 3A) and exert a removal force, in the direction of arrow R (see FIG. 3B), on the sheath 42 tending to biases the sheath 42 laterally along the longitudinal axis A of the syringe 4 and hypodermic needle 26. The removal force R continues building until this force is greater than the retention force between the sheath 42 and the exterior surface of the hub 28.

Figure 4B:
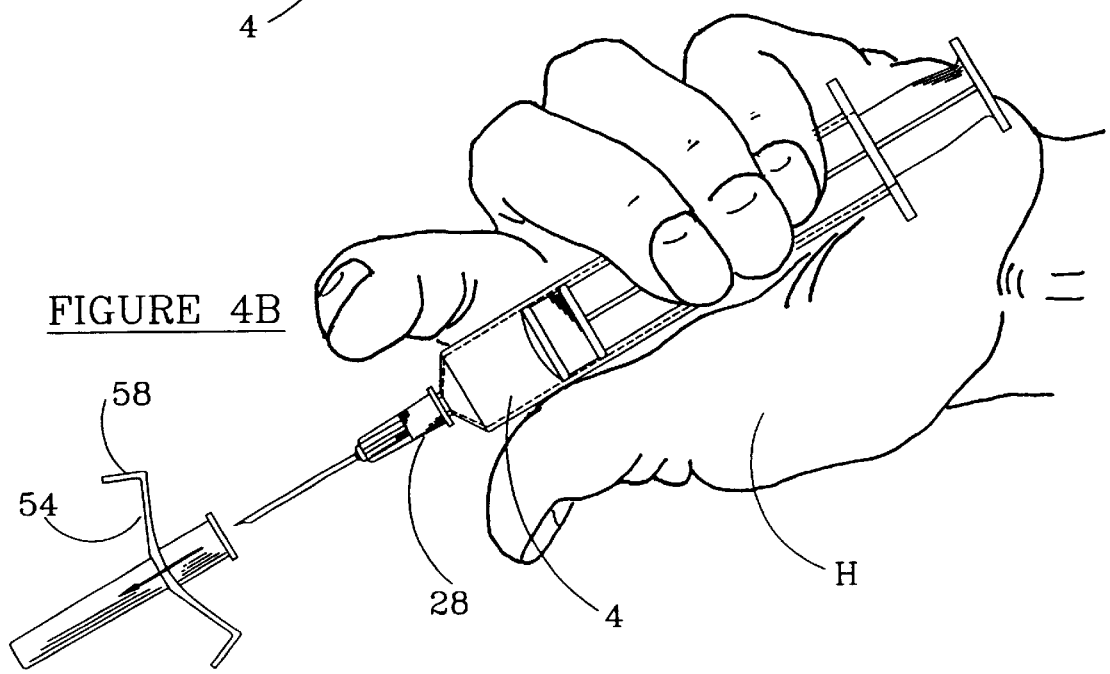
FIG. 4B is a diagrammatic perspective view showing the improved sheath being expelled from the hypodermic needle following generation of a sufficient removal force.

Once the removal force R is significantly greater than the frictional connection force between the proximal end 44 of the sheath 42 and the hub 28 of the hypodermic needle 26, the sheath 42 is thrusted toward the right (as can been seen in FIG. 3B and the left as can be seen in FIG. 4B) away from the hub 28 and the hypodermic needle 26 thereby causing rapid relative movement between the sheath 42 and hypodermic needle 26. This thrust action generally results from the tensions legs 56 returning back to their normal straight configuration (see FIGS. 1 and 2) while the pushing surfaces 58 are still pressed inwardly by the thumb and index finger of the clinician generating the removal force R. The resulting removal force R tends to be in a direction which extends parallel to the longitudinal axis A of the syringe 4 and hypodermic needle 26, thereby facilitating removal the sheath 42 from the hypodermic needle 26 without contacting and/or damaging the hypodermic cannula shaft 30 or hypodermic tip or point 32. As a result of the improved sheath removal system, the clinician is able to remove the sheath 42 from the hypodermic needle 26 via a "one handed technique" while still minimizing the possibility of an inadvertent needle stick occurring to either the clinician, the patient or some other proximate care giver.

Figure 5A:
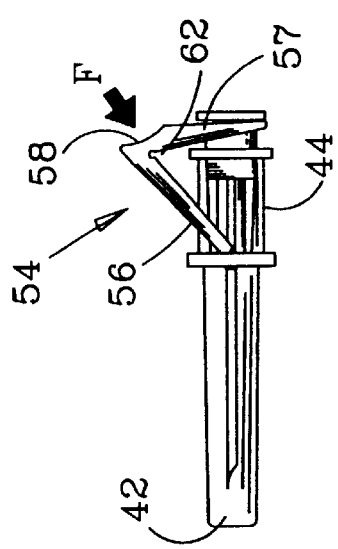
FIG. 5A is a partial diagrammatic assembled side elevational view of a second embodiment of the improved sheath shown coupled to a hypodermic needle.
Figure 5B:
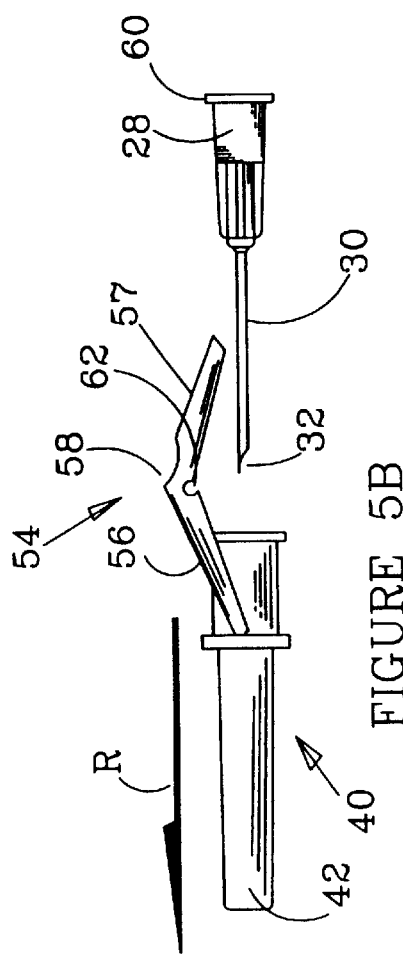
FIG. 5B is a diagrammatic side elevational view of the second embodiment showing the sheath being expelled axially along the hypodermic needle following generation of a sufficient removal force.

With reference now to FIGS. 5A and 5B, a detailed description concerning a second embodiment of the sheath removal system 40 will now be described. As this embodiment is similar to the first embodiment in many respects, only the difference between this embodiment and the first embodiment will be discussed in detail.

The basic difference between this embodiment and the prior embodiment is the shape and orientation of the appendage 54. According to this embodiment, only a single appendage 54 is utilized. The single appendage 54 includes first and second tension legs 56 and 57, with the first tension leg 56 connected to the proximal end 44 of the sheath 42 while the second tension leg 57 is located to releasably engage with or abut against an annular flange 60 of the hub 28. An intermediate portion of the appendage 54 is provided with the pushing surface 58 and a living hinge 62 is provided on a surface opposite to the pushing surface 58. The living hinge 62 facilitates a bending movement between the first and second legs 56 and 57.

According to this embodiment, when a clinician exerts a removal force R by placing one of his or her index finger or thumb on the first pushing surface 58 and the other of his or her index finger and thumb on the hub 28 and pinches his or her index fingers and thumb toward one another, as indicated by arrows F, the pushing surface 58 moves toward the hub 28/proximal end 44 of the sheath and the first and second tension legs 56 and 57 tend to bow and commence generation of a removal force R on the sheath 42. Once the removal force R increases and surpasses the friction retention force between the sheath 42 and the hub 28, the sheath is thrusted axially along the longitudinal axis A of the hypodermic needle 26 in the direction of arrow R (to the left as can be seen in FIG. 5B).

Figure 6A:
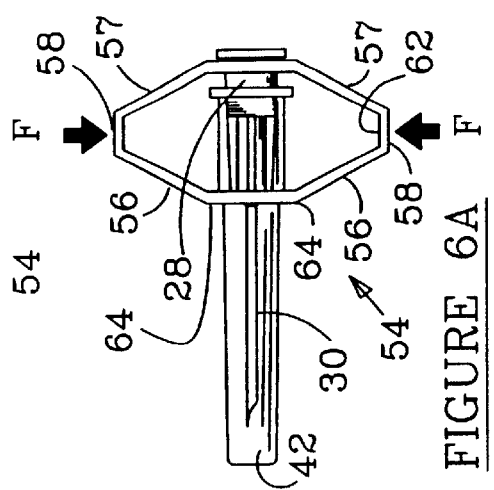
FIG. 6A is a partial diagrammatic assembled side elevational view of a third embodiment of the improved sheath shown coupled to a hypodermic needle.
Figure 6B:
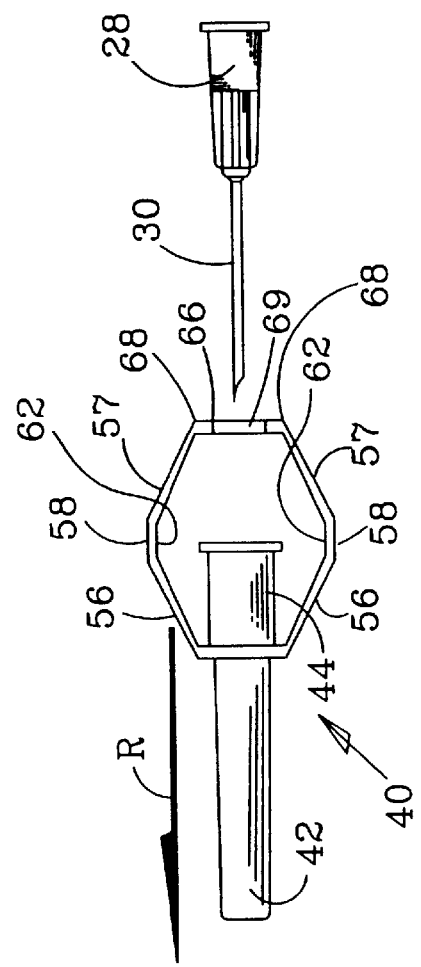
FIG. 6B is a diagrammatic side elevational view of the third embodiment showing the sheath being expelled axially along the hypodermic needle following generation of a sufficient removal force.

With reference now to FIGS. 6A and 6B, a detailed description concerning a third embodiment of the sheath removal system, according to the present invention, will now be described. As this embodiment is similar to the second embodiment in many respects, only the difference between this embodiment and the second embodiment will be discussed in detail.

This embodiment is similar to the second embodiment except a pair of opposed appendages 54 are provided. Each one of the opposed appendages 54 comprises first and second legs 56 and 57 which are connected together via a living hinge 62. An end of the first tension leg 58, remote from the living hinge 62, is connected to sheath 42 via a first flexible hinge 64 and an end of the second tension leg 57, remote from the living hinge 62, is connected to a shroud 66 via a second flexible hinge 68. The shroud 66 has a cylindrical aperture 69 which is sized to receive and matingly engage with the hub 28 of the hypodermic needle 26.

When a clinician desires to remove the sheath 42, the clinician presses his or her index finger against a first one of the pushing surfaces 58 and presses the other of his or her thumb and index finger against the second pushing surface 58 to pinch the two pushing surfaces 58 toward one another, as indicated by arrows F. As a result of such motion, the first and second tension legs 58 and 59 commence to bow and exert a removal force R on the sheath 42 tending to propel the sheath 42 axially along the hypodermic needle 26 parallel to the longitudinal axis A. As the clinician continues pinching the two pushing surfaces 58 toward one another, the removal force R gradually increases until it surpasses the retention friction force between the sheath 42 and the exterior surface of the hub 28. Once this occurs, the sheath 42 is thrusted longitudinally along the longitudinal axis A of the hypodermic needle 26 removing the sheath 42, and the attached appendages 54, from the hypodermic needle 26.

Figure 7A:
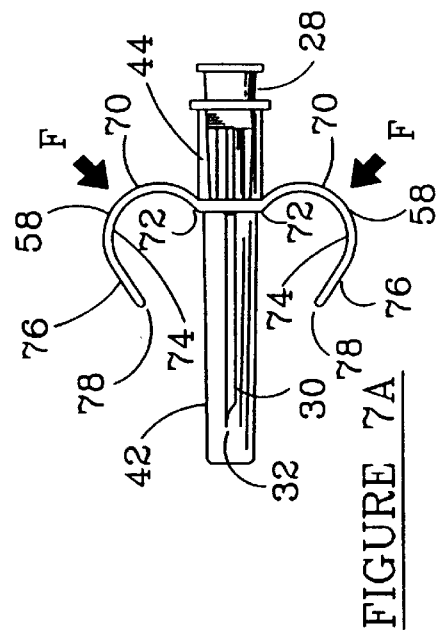
FIG. 7A is a partial diagrammatic assembled side elevational view of a fourth embodiment of the improved sheath shown coupled to a hypodermic needle.
Figure 7B:
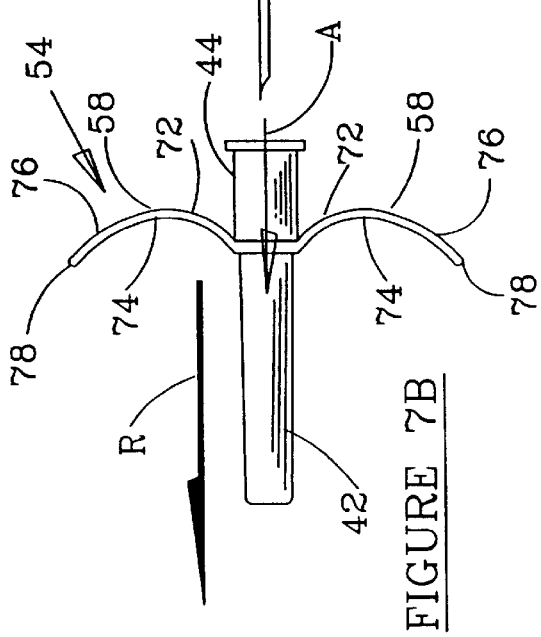
FIG. 7B is a diagrammatic side elevational view of the fourth embodiment showing the sheath being expelled axially along the hypodermic needle following generation of a sufficient removal force.

With reference now to FIGS. 7A and 7B, a detailed description concerning a fourth embodiment of the sheath removal system, according to the present invention, will now be described. As this embodiment is similar to the first embodiment in many respects, only the difference between this embodiment and the first embodiment will be discussed in detail.

FIG. 7A shows a fourth embodiment in which the appendage 54 comprises a pair of curved C-shaped appendages 70. Each curved C-shaped appendage 70 generally comprises a tension leg 72 connected to the proximal end 44 of the sheath 42. An intermediate area 74 of an outwardly facing surface 76 of each of the C-shaped curved appendages 70 forms a respective pushing surface 58. A remote end 78 of each of the C-shaped curved appendages 70 is free and is not connected to the sheath 42.

When a clinician desires to remove the sheath 42, the clinician presses his or her index finger against one of the pushing surfaces 58 and presses his or her thumb against the other pushing surface 58 to pinch the two pushing surfaces 56 toward one another, as indicated by arrows F. As a result of such motion, the two tension legs 72 commence generation of a removal force R on the sheath 42 tending to move or propel the sheath 42 axially along the longitudinal axis A of the hypodermic needle 26. As the clinician continues pinching the two pushing surfaces 56 toward one another, the removal force R gradually increases until it surpasses the retention friction force between the sheath 42 and the exterior surface of the hub 28.

Once this occurs, the sheath 42 is thrusted longitudinally along the longitudinal axis A of the hypodermic needle 26 to remove the sheath 42, and the attached appendages 54, from the hypodermic needle 26 (see FIG. 7B). During such removal action, the curved C-shaped members re-expand back to their original undeformed shape (see FIG. 7B).

Figure 7D:
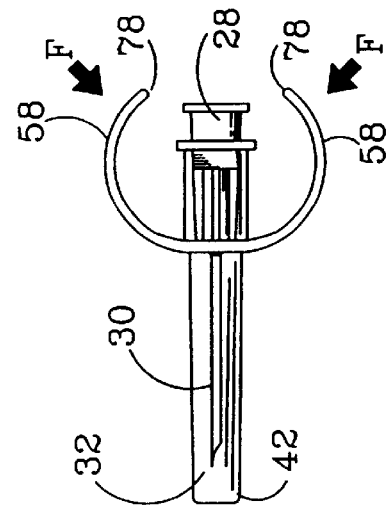
FIG. 7D is a partial diagrammatic assembled side elevational view of a sixth embodiment of the improved sheath, somewhat similar to the fourth embodiment, shown coupled to a hypodermic needle.
Figure 7C:
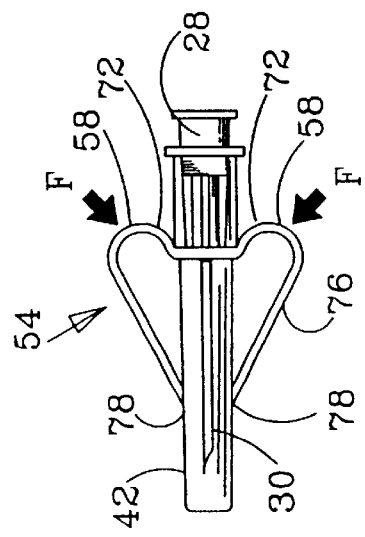
FIG. 7C is a partial diagrammatic assembled side elevational view of a fifth embodiment of the improved sheath, somewhat similar to the fourth embodiment, shown coupled to a hypodermic needle.

With reference now to FIG. 7C, a detailed description concerning a fifth embodiment of the sheath removal system will now be described. As this embodiment is similar to the fourth embodiment in many respects, only the difference between this embodiment and the fourth embodiment will be discussed in detail.

The fifth embodiment of FIG. 7C is very similar to the fourth embodiment. The only notable difference is that the remote extensions 78 of each of the C-shaped curved appendages 70 is connected to an intermediate portion of the sheath 42, rather than being free as with the fourth embodiment. In all other respects, this embodiment is substantially identical to the fourth embodiment.

According to this embodiment, when a clinician desires to remove the sheath 42, the clinician presses his or her index finger against one of the pushing surfaces 58 and presses his or her thumb against the other pushing surface 58 to pinch the two pushing surfaces 58 toward one another, as indicated by arrows F. As a result of such motion, the two tension legs 72 as well as the remotely connected extensions 80 commence generation of a removal force R on the sheath 42 tending to move or slide the sheath 42 axially along the longitudinal axis A of the hypodermic needle 26. As the clinician continues pinching the two pushing surfaces 58 toward one another, the removal force R gradually increases until it surpasses the retention friction force between the sheath 42 and the exterior surface of the hub 28.

Once this occurs, the sheath 42 is thrusted longitudinally along the longitudinal axis A of the hypodermic needle 26 to remove the sheath 42, and the attached appendages 54, from the hypodermic needle 26 (not shown). During such removal action, the curved C-shaped members 70 re-expand back to their original undeformed shape.

With reference now to FIG. 7D, a detailed description concerning a sixth embodiment of the sheath removal system will now be described. As this embodiment is similar to the fourth embodiment in many respects, only the difference between this embodiment and the fourth embodiment will be discussed in detail.

The sixth embodiment of FIG. 7D is very similar to the fourth embodiment. The only notable difference is the variation in the shape and orientation of each of the C-shaped curved appendages 70. That is, each of the curved C-shaped appendage 70 generally comprises a tension leg 72 connected to the proximal end 44 of the sheath 42. An intermediate area 74 of an outwardly facing surface 76 of each of the C-shaped curved appendages 70 forms a respective pushing surface 58. A remote end 78 of each of the C-shaped curved appendages 70 is free but extends toward the proximal end of the sheath 42 and is not connected to the sheath 42. In all other respects, this embodiment is substantially identical to the fourth embodiment.

According to this embodiment, when a clinician desires to remove the sheath 42, the clinician presses his or her index finger against one of the pushing surfaces 58 and presses his or her thumb against the other pushing surface 58 to pinch the two pushing surfaces 58 toward one another, as indicated by arrows F. As a result of such motion, the two tension legs 72 as well as the remotely connected extensions 80 commence generation of a removal force R on the sheath 42 tending to move or slide the sheath 42 axially along the longitudinal axis A of the hypodermic needle 26. As the clinician continues pinching the two pushing surfaces 58 toward one another, the removal force R gradually increases until it surpasses the retention friction force between the sheath 42 and the exterior surface of the hub 28.

Once this occurs, the sheath 42 is thrusted longitudinally along the longitudinal axis A of the hypodermic needle 26 to remove the sheath 42, and the attached appendages 54, from the hypodermic needle 26 (not shown). During such removal action, the curved C-shaped members 70 re-expand back to their original undeformed shape.

Figure 8A:
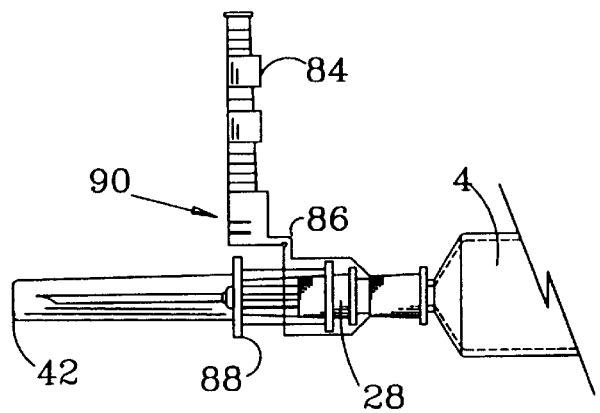
FIG. 8A illustrates a diagrammatic side view of a seventh embodiment in which the sheath removal means is incorporated into a needle safety cover.
Figure 8B:
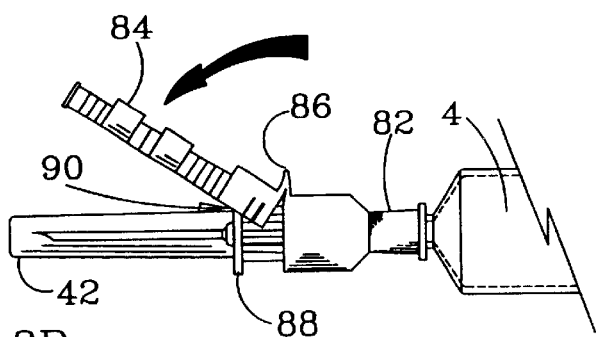
FIG. 8B illustrates a diagrammatic view of the seventh embodiment with the safety cover rotated to engage the needle sheath removal mechanism with the needle sheath.
Figure 8C:
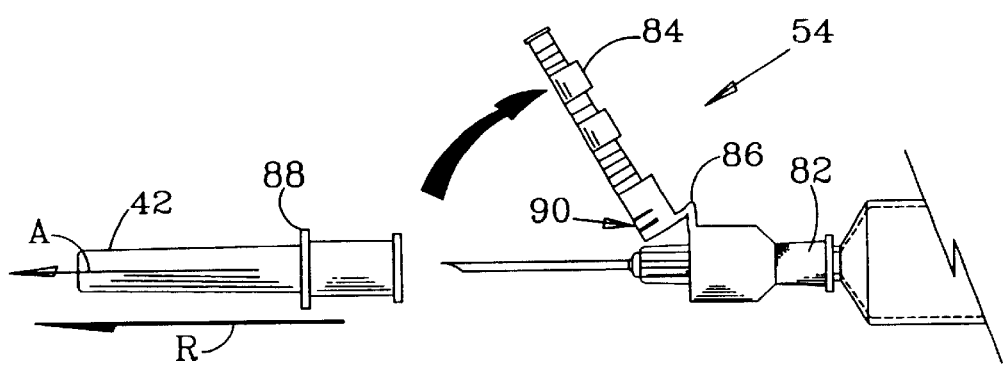
FIG. 8C illustrates a diagrammatic side view of the seventh embodiment with the safety cover spring back disengaging the sheath from the hypodermic needle.

With reference to FIGS. 8A–8C, a seventh embodiment of the present invention will now be briefly discussed. According to this embodiment, the appendage comprises an annular housing 82 which surrounds and matingly engages with the hub 28 of the hypodermic needle 26. A leg 84 is connected to the annular housing 82 by a pivot hinge 86. The pivot hinge 86 facilitates pivoting motion of the leg 84 relative to the annular housing 82 from a position in which the leg 84 extends substantially parallel to the longitudinal axis A of the hypodermic needle 26, following use of the hypodermic needle 26 (not shown), to a position in which the leg 84 extends perpendicular to the longitudinal axis A of the hypodermic needle 26 (see FIG. 8A).

The sheath 42 is equipped with an annular flange 88 while the leg 84 of the appendage 54 is equipped with an internal mating pushing notch, rib flange or some other member 90. The annular housing 82 is provided with a levering mechanism so that as the leg 84 is pivoted from the position in FIG. 8A toward the position in FIG. 8B, the pushing member 90 engages with the annular flange 88 and commences exertion of a biasing force on the sheath 42 tending to force the sheath in the direction of arrow R along the longitudinal axis A. Once the leg 84 is pivoted about 45 degrees or so, to the position shown in FIG. 8B, the pushing member 90 "snaps" behind the annular flange 88. Once this occurs, the pushing member 90 is then located to exert a lever action on the annular flange 88 and eject the sheath 42 from the needle 32 upon the leg 84 being returned back to its initial position shown in FIG. 8A.

According to this embodiment, when a clinician desires to remove the sheath 42, the clinician first rotates or pivots the leg 84 from the position show in FIG. 8A toward the position shown in FIG. 8B. During such pivoting motion, the internal mating pushing member 90 becomes engaged with the annular flange 88 of the sheath 42 and snap behind the pushing member 90. Once this occurs, the clinician then returns the leg 84 from the position show in FIG. 8B toward the position shown in FIG. 8A. Due to this return motion, the living hinge is under tension and exerts a removal force R on the sheath 42 (see FIG. 8C) tending to eject or expel the sheath 42 axially along the longitudinal axis A of the hypodermic needle 26 and completely remove the sheath 42, and the attached appendage 54, from the hypodermic needle 26.

Figure 9:
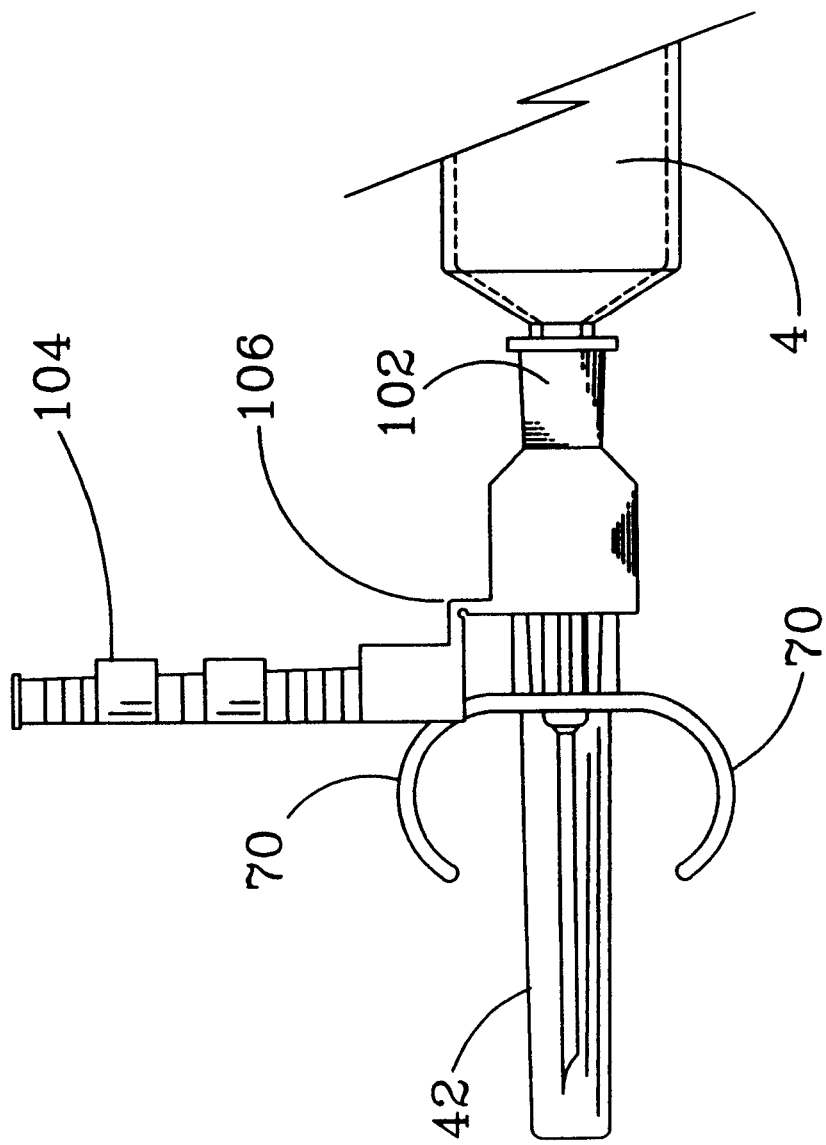
FIG. 9 illustrates a diagrammatic side view of the fourth embodiment in combination with a prior art, post use sharps safety protection device.

With reference now to FIG. 9, a brief description concerning use of the fourth embodiment of the sheath removal system, according to the present invention, in combination with a conventional post use, sharps safety protection device 100 will now be described. As this embodiment is similar to the fourth embodiment in many respects, only the difference between this embodiment and the first embodiment will be discussed in detail.

The post use, sharps safety protection device 100 comprises an annular housing 102 which surrounds and matingly engages with the hub 28 of the hypodermic needle 26. A protective leg 104 is connected to the annular housing 102 by a pivot hinge 106. The pivot hinge 106 facilitates pivoting motion of the protective leg 104 relative to the annular housing 102 from a position in which the protective leg 104 extends perpendicular to the longitudinal axis A of the hypodermic needle 26 (see FIG. 9), to a position in which the protective leg 104 extends substantially parallel to the longitudinal axis A of the hypodermic needle 26, following use of the hypodermic needle 26 (not shown).

Once the sheath 42 is automatically removed, by the sheath removal system according to the present invention, the clinician then uses the hypodermic needle 26 in a conventional fashion. Following use of the hypodermic needle 26, the clinician rotates or pivots the protective leg 104, relative to the annular housing 102, from a position in which the protective leg 104 extends perpendicular to the longitudinal axis A of the hypodermic needle 26 (see FIG. 9) to a position in which the protective leg 104 extends substantially parallel to the longitudinal axis A (not shown) to encase and/or surround the hypodermic needle 26 and the needle tip 28. The protective leg 104, when in this encasing position, covers the needle tip 28 and prevents an inadvertent needle stick from the used needle while the hypodermic needle is being during disposal of the same by the clinician or other personnel.

It is to be appreciated that the various components of the sheath removal system can be manufactured from a plastic material, such as polypropylene, styrene, or other some other conventional material.

Since certain changes may be made in the above described automated sheath removal system and associated method, without departing from the scope of the invention here involved, it is intended that all of the subject matter relating to the above description and shown in the accompanying drawings shall be interpreted as merely examples illustrating the inventive concept herein, and shall not be construed as limiting the invention.

I claim:

1. A removal system to facilitate removal of a sheath from a medical device by an operator using one hand, the medical device defining a longitudinal axis, the removal system comprising:

a sheath having an exterior housing defining an internal cavity for accommodating a medical device therein, the sheath being open at least one end thereof to facilitate receiving at least a portion of the medical device within the exterior housing;

an exterior surface of the sheath supporting at least one appendage thereof, and the at least one appendage, once a sufficient force is applied thereto, inducing movement of the sheath along the longitudinal axis, in a direction away from the medical device, to facilitate automatic removal of the sheath from the medical device solely by actuation of the at least one appendage; and the at least one appendage is adapted such that force applied substantially perpendicularly to the longitudinal axis induces a force in the sheath directed along the longitudinal axis in a direction away from the medical device thereby facilitating removal of the sheath from the medical device.

2. The removal system according to claim 1, wherein the medical device is a hypodermic needle and the appendage comprises at least one tension leg which, at least partially, bows when force is applied to the appendage.

3. The removal system according to claim 1, wherein a pair of appendages are provided to facilitate removal of the sheath, each one of the pair of appendages comprises a pushing surface and a tension leg interconnects the pushing surface with a proximal end of the sheath, and the tension legs facilitate generating a thrusting force on the sheath, once the pushing surfaces are sufficiently biased towards one another, to thrust the sheath longitudinally along the longitudinal axis, defined by the medical device, to remove the sheath from the medical device while minimizing possible damage to the medical device.

4. The removal system according to claim 3, wherein each one of the pushing surfaces extends substantially one of parallel, perpendicular and inclined with respect to a longitudinal axis defined by the sheath.

5. The removal system according to claim 1, wherein the sheath is generally tubular in shape and is open at one end thereof, and the sheath defines an interior cavity for accommodating a hypodermic needle.

6. The removal system according to claim 5, wherein the sheath has a diameter of between 0.050 and 0.075 inches and has an axial length of between 0.060 and 6 inches.

7. The removal system according to claim 6, wherein the sheath has an exterior wall thickness of between 0.025 and 0.500 inches.

8. The removal system according to claim 1, wherein the sheath is manufactured from one of polypropylene, polyethylene and styrene.

9. The removal system according to claim 1, wherein the at least one appendage comprises first and second tension legs which are connected to one another by a living hinge to facilitate relative pivoting motion between the first and second tension legs and the first tension leg is affixed to the sheath while the second tension leg is engageable with the medical device.

10. The removal system according to claim 1, wherein a pair of appendages are provided and each one of the appendages comprises first and second tension legs which are connected to one another by a living hinge to facilitate relative pivoting motion between the first and second tension legs and the first tension leg of each appendage is also affixed to a proximal end of the sheath while the second tension leg is also affixed to a shroud for engaging with the medical device.

11. The removal system according to claim 10, wherein the appendage comprises an annular housing which surrounds and matingly engages with a hub of the medical device, and a pivot leg is connected to the annular housing by a pivot hinge, and the pivot hinge facilitates pivoting motion of the leg relative to the annular housing from a position in which the leg extends parallel to a longitudinal axis of the medical device to a position in which the leg extends perpendicular to the longitudinal axis of the medical device, the sheath is equipped with an annular flange while the leg is equipped with an internal mating gripping flange, and the annular housing is provided with a spring mechanism so that when the sheath is moved axially along the longitudinal axis, toward a hub of the medical device, the spring becomes partially compressed.

12. A removal system to facilitate removal of a sheath from a medical device by an operator using one hand, the medical device defining a longitudinal axis, the removal system comprising:

a sheath having an exterior housing defining an internal cavity for accommodating a medical device therein, the sheath being open at least one end thereof to facilitate receiving at least a portion of the medical device within the exterior housing;

an exterior surface of the sheath supporting at least one appendage thereof, and the at least one appendage, once a sufficient force is applied thereto, inducing movement of the sheath along the longitudinal axis, in a direction away from the medical device, to facilitate automatic removal of the sheath from the medical device solely by actuation of the at least one appendage; and a pair of appendages are provided to facilitate removal of the sheath, each one of the pair of appendages comprises a generally C-shaped appendage with a pushing surface, and a tension leg interconnects the pushing surface with a proximal end of the sheath, and the tension leg facilitates generating a thrusting force on the sheath, once the pushing surfaces are sufficiently biased towards one another, to thrust the sheath longitudinally along the longitudinal axis, defined by the medical device, to remove the sheath from the medical device while minimizing possible damage to the medical device.

13. The removal system according to claim 12, wherein a free end of each of the C-shaped curved appendages is unconnected to the sheath.

14. The removal system according to claim 12, wherein a remote end of each of the C-shaped curved appendages is connected to an intermediate portion of the sheath.

15. A removal system to facilitate removal of a sheath from a hypodermic needle by an operator using one hand, the hypodermic needle defining a longitudinal axis, the removal system comprising:

a sheath having an exterior housing defining an internal cavity for accommodating a hypodermic needle therein, and the sheath being open at least one end thereof to facilitate receiving a hypodermic needle therein;

an exterior surface of the sheath supporting at least one appendage thereof, the at least one appendage comprising at least one tension leg which interconnects a pushing surface with the sheath, the at least one tension leg partially bows, once a sufficient removal force is applied thereto to induce movement of the sheath along the longitudinal axis, in a direction away from the hypodermic needle, to facilitate automatic removal of the sheath from the hypodermic needle solely by actuation of the at least one appendage; and p1 the at least one appendage is adapted such that force applied substantially perpendicularly toward the longitudinal axis of the hypodermic needle is directed along the longitudinal axis in a direction facilitating removal of the sheath from the hypodermic needle.

16. The removal system according to claim 15, wherein the sheath is generally tubular in shape and is open at one end thereof, and the sheath defines an interior cavity for accommodating the hypodermic needle;

the sheath has a diameter of between 0.050 and 0.075 inches and has an axial length of between 0.060 and 6 inches; and the sheath has an exterior wall thickness of between 0.025 and 0.500 inches; and the sheath is manufactured from one of polypropylene, polyethylene and styrene.

17. A method of facilitating removal of a sheath from a medical device by an operator using one hand the method comprising the steps of:

defining a longitudinal axis with the medical device;

providing a sheath with an exterior housing defining an internal cavity for accommodating a medical device therein, and the sheath being open at least one end thereof to facilitate receiving a medical device therein;

supporting at least one appendage by an exterior surface of the sheath;

once a sufficient force is applied thereto, the at least one appendage inducing movement of the sheath along the longitudinal axis, in a direction away from the medical device, to facilitate automatic removal of the sheath from the medical device solely imply by actuation of the at least one appendage; and applying a force to the at least one appendage substantially perpendicularly to the longitudinal axis of the sheath so that the at least one appendage induces movement of the sheath along the longitudinal axis in a direction away from the medical device to facilitate removal of the sheath from the medical device.

* * * * *